United States Patent [19]

Silver et al.

[11] Patent Number: 4,906,575
[45] Date of Patent: Mar. 6, 1990

[54] PHOSPHATE COMPOUND THAT IS USED IN A MICROBIAL PROFILE MODIFICATION PROCESS

[75] Inventors: Richard S. Silver, Allentown; Pamela M. Bunting, Cheswick, both of Pa.

[73] Assignee: Chevron Research Company, San Francisco, Calif.

[21] Appl. No.: 23,070

[22] Filed: Mar. 6, 1987

[51] Int. Cl.$^4$ .............................. C12N 1/12; C12R 1/01
[52] U.S. Cl. .................................. 435/253.6; 435/243; 435/252.1; 435/254; 435/257; 435/258
[58] Field of Search .................. 435/243, 252.1, 253.6, 435/254, 257, 258

[56] References Cited

U.S. PATENT DOCUMENTS

| | | | |
|---|---|---|---|
| 2,844,515 | 7/1958 | Sobotka et al. | 435/253.6 |
| 4,010,071 | 3/1977 | Colegrove | 435/274 |
| 4,266,031 | 5/1981 | Tang et al. | 435/188 |
| 4,460,043 | 7/1984 | Thompson et al. | 166/246 |
| 4,658,898 | 4/1987 | Paul et al. | 166/270 |

OTHER PUBLICATIONS

Stecher, Ed., *The Merck Index*, Eighth Edition, 1968, p. 968.
Valikhanov et al., "Assimilation of Phosphorus from Condensed Phosphates by Sprouts of Some Higher Plants," Uzb. Biol. Zh. 0(5): 27-29, 1980, (BA 73: 13148).

*Primary Examiner*—Robert A. Wax
*Attorney, Agent, or Firm*—E. J. Keeling; E. A. Schaal

[57] ABSTRACT

The present invention is a phosphate compound for use in a bacterial nutrient medium. The medium is injected downhole in a petroleum formation along with a bacteria (or its spore) and provides the bacteria with growth nutrients. The nutrient solution contains a phosphate compound which: will not precipitate out of solution under ambient conditions; will chelate alkaline earth, rare earth, transition and heavy metal ions; and provide a nutrient source for the bacteria.

12 Claims, No Drawings

PHOSPHATE COMPOUND THAT IS USED IN A MICROBIAL PROFILE MODIFICATION PROCESS

U.S. Ser. No. 022,857, filed Mar. 6, 1987, entitled "Bacteria and its Use in a Microbial Profile Modification Process" (now abandoned in lieu of U.S. Ser. No. 140,892); U.S. Ser. No. 023,063, filed "Bacteria and Method of Isolation for Use in a Microbial Profile Modification Process"; and U.S. Ser. NO. 140,892, filed Dec. 29, 1987, entitled "Bacteria and its Use in a Microbial Profile Modification Process" (now U.S. Pat. No. 4,799,545, which issued on Jan. 24, 1989).

BACKGROUND OF THE INVENTION

This invention generally relates to the use of microorganisms to enhance oil recovery from petroleum reservoirs. Here, a specific phosphate compound is used to serve as a nutrient source and a chelation agent for metal ions.

Petroleum that is in underground reservoirs is brought to the surface in a variety of ways. One of the more notable publicly held ideas of oil recovery is the "gusher," however, due to the changing nature of oil reserves, and economic and environmental policies, the gusher is the thing of the past. Surface pumps, which are a common highway sight, oftentimes provides the lift force necessary to bring oil to the surface in those reservoirs where the overburden pressure is insufficient. Additionally, subsurface pumps can be coupled with the surface pumps to assist in the lifting duty. However, there comes a time in the life of many reservoir formations in which the overburden pressure and the pumping devices are not enough to overcome the oil viscosity and the capillary forces of the formation. At this point, enhanced oil recovery (EOR) techniques are useful to drive out that stubborn quantity of oil that refuses to come to the surface by the means described above.

The term "EOR" spans a panoply of techniques and devices that are used to recover the last bit of oil reserves. There are devices and methods for: steam injection, water injection, gas driving, emulsifying, injecting plugging agents, etc. One "device" that may perform many of these feats is a microorganism, most notably, a bacteria.

The idea of using bacteria to increase or enhance oil recovery is not new. Many laboratory investigations and a number of field tests have been performed both in the U.S. and elsewhere (see generally J. Davis, Petroleum Microbiology (1967) and works collected in J. E. Zajic et al., Microbes and Oil Recovery, Bioresource Publications, El Paso (1985). Several technical meetings devoted exclusively to microbial enhanced oil recovery (MEOR) have been held. Some of the previous literature consists of anecdotal accounts or inadequately controlled studies, resulting in a skeptical appraisal of the technology. (See also D. Hitzman, "Petroleum Microbiology and the History of its Role in Enhanced Oil Recovery," Proc. Int'l. Conf. on Micro. Enh. Oil Rec., p 162 (May 1621, 1982), and E. Donaldson et al., "There are Bugs in My Oil Well," Chemtech, p 602 (Oct. 1985).)

The principle behind MEOR is basd on the fact that microbes can produce most of the agents now employed in chemical EOR; i.e., water-soluble polymers, surfactants, co-surfactants and solvents such as ethanol and acetone, and acids. (See M. Singer, Microbial Biosurfactants, in Zajic, Microbes and Oil Recovery; U.S. Patent No. 4,522,261 to McInerney et al.; U.S. Patent No. 2,807,570 to Updegraff and U.S. Patent No. 2,660,550 to Updegraff et al.) Some microbial-produced products, e.g., xanthan biopolymer, are now commercially used for EOR. Such use is dependent on the cost-effectiveness of the microbial product compared to competing non-microbial products, e.g., xanthan compared to polyacrylamide. In this application, the definition of MEOR applies to processes involving the in-situ application of microbial processes and usually excludes EOR processes which merely involve the use of chemical products which are produced in a fermentation plant.

The specific application of microorganisms for EOR in this invention is their use for the selective plugging of zones of high permeability (i.e., thief zones) in petroleum reservoirs. To back up a bit, when water injection is used to recover oil, it is injected downhole in an injection well to move any oil out of the formation to be recovered at a producing well. The water pushes the oil out of the small interstices and pores of the rocks, but it pushes the oil out of wider spaces ad larger pores (i.e., zones of higher permeability) first, leaving the smaller areas still filled with oil. Since petroleum is formed in stratified sedimentary deposits, several distinct layers of oil-bearing sands are usually present over the vertical profile of an oil well. Different layers can vary widely in permeability and porosity, as well as other properties. Since a waterflood will naturally seek the zone of least resistance (or highest permeability), low permeability zones may be bypassed. After a time, recoverable oil is "watered out" of the high permeability zones, but the low permeability streaks still contain considerable recoverable oil. The way that the residual oil may be taken out of these lower permeability zones is by "profile modification". Current technology involves the injection of water-soluble polymers, which selectively enter the high permeability zones. Cationic cross-linking agents, i.e., $Cr^{+3}$ or $+6$, $Ti^{+4}$, or $Al^{+3}$, held in solution by a complexing agent (i.e., citrate) or by oxidation state, are co-injected with the polymer or are swept after the polymer. (See U.S. Patent No. 4,552,217 to Wu et al.) As the polymer gradually cross-links and gels into a water-insoluble 3-D matrix in the high permeability zones, the waterflood is channeled into zones of low permeability, thus increasing oil production. There are problems associated with the techniques of profile modification with cross-linking polymers. Such polymers are relatively expensive; they may shear-degrade upon injection at the wellhead and may not penetrate sufficiently before gelling. For this reason, the use of microorganisms may provide promising in profile modification because it may eliminate some of these problems.

As with other techniques, using microbes to plug high permeability zones is not exactly new. Some early researchers are listed in J. Davis, "Petroleum Microbiology" (1967) and more recently there is U.S. Patent No. 4,558,739 to McInerney et al.; and D. Revus, "A Study of Reservoir Selective Plugging Utilizing In Situ Growth of Bacteria to Improve Volumetric Sweep Efficiency, "Masters Thesis, University of Oklahoma (1982); P. Kalish et al., "The Effect of Bacteria on Sandstone Permeability, "16 Jour. Pet. Tech 805 (July 1964); and C. Brierly et al, "Investigations of Microbially Induced Permeability Loss During In-Situ Leaching,"

Bureau of Mines (NTIS Publication) (April 1982). They use microbes in a variety of ways to enhance oil recovery. Some researchers have used the bacteria that naturally exists in the formation and have simply injected nutrients downhole to get them to grow and plug the formation (see U.S. Patent No. 4,475,590 to Brown; and L. Allison, "Effect of Microorganisms on Permeability of Soil Under Prolonged Submergence," 63 Soil Science 439 (1947)). Others have injected bacteria downhole and then followed by a nutrient solution. On another score, some researchers depend on the biomass of the bacteria for plugging purposes, while others show that exopolymers produced by the bacteria are effective in closing off areas of high permeability.

Another factor in this plugging technique is the size of the organism that is being injected. For example, if a bacteria has a small enough size, it may penetrate the formation a bit easier to plug off the thief zones. To that end, the spores of different bacteria may be used for injection to penetrate even deeper. Spores penetrate a reservoir formation easier and become lodged in the permeable zones, so that when they are stimulated to grow by a nutrient solution, they will plug more pores more effectively. To better achieve penetration, vegetative cells arising by germination of the spores should be motile so that they may propel themselves deeper into the pores.

Some problems exist with the environment in which the bacteria are injected. For example, downhole in a petroleum reservoir, there are conditions that put constraints on microorganisms. More specifically, connate water, in many formations, has both high concentrations of salt (NaCl), alkaline earth ions ($Ca^{+2}$, $Mg^{+2}$, $Ba^{+2}$), rare earth, transition metals, and heavy metal ions. Such ions can form insoluble precipitates with many of the standard components of bacterial nutrient media. The most important for purposes of this application is phosphate. These alkaline earth metal ions are especially troublesome because they precipitate phosphate out of the medium. This plugs the wellbore and prevents the injection of cells or nutrients as well as removing the phosphate (as a nutrient source) from the bacteria. Furthermore, some of these ions are inhibitory or toxic to microbial cells and we have found that some ions (eg., $Ca^{+2}$) are inhibitory to biopolymer production by our microorganisms. Bacteria that are injected downhole must be tolerant to these if they are to survive.

The downhole environment is usually anoxic, unlike the highly oxygenated condition above. To be able to survive and live in both environments, a bacteria must either be shielded from oxygen (which may be difficult and expensive) or must be tolerant to it (e.g., a facultative anaerobe). [Bacteria can be broadly divided into 3 categories based on their ability to utilize and tolerate oxygen: (1) obligate aerobic bacteria, which require molecular oxygen for growth; (2) obligate anerobic bacteria, to which molecular oxygen is toxic; and (3) facultative anaerobic bacteria, which can grow either in the presence or absence of atmospheric oxygen. Of the three, facultative anaerobes appear to be the most suitable MEOR candidates, since they can survive exposure to air during storage and injection while retaining the ability to grow well anaerobically.]

The most important ingredient, i.e., the bacteria, sometimes must be selected for these exact conditions that exist in a reservoir. Also, the nutrient's solution has to be tailored to both the bacteria and the reservoir in which it has to be injected. All these considerations must be merged together to provide the desired result in plugging the formation.

Once these problems have been conquered, the bacteria must be stimulated to grow and produce an exopolymer. However, due to the harsh conditions it is very difficult to provide the appropriate growth medium. For example, some nutrients may complex with compounds that are found in-situ and may precipitate out of solution. For example, bacteria require the element phosphorous as an essential nutrient and the most commonly used source are ortho phosphate salts such as sodium or potassium mono or dibasic phosphate. However, such phosphate salts precipitate when they encounter sufficient concentrations of polyvalent metal ions, such as $Al^{+3}$ or $Cr^{+3}$ or alkaline earth metal ions such as $Ca^{+2}$, $Mg^{+2}$ or $Ba^{+2}$. If and when the phosphates precipitate out of solution, they are rendered useless to the bacteria so that growth will be limited. Further, such precipitates plug the wellbore and render further injection of cells or nutrient impossible.

OBJECTS OF THE INVENTION

It is an object of this invention to develop a nutrient solution that may be injected downhole in a petroleum reservoir to insure that injected bacterial spores used for Microbial Enhanced Oil Recovery, mature and grow into vegetative cells and produce a biopolymer.

More specifically, it is an object of this invention to provide a phosphate source for a MEOR bacteria that will not precipitate out of solution when it is contacted with heavy metal, alkaline earth, rare earth, or transition metal ions. It is a further object of this invention to provide a chelating agent to hold heavy metal ions in solution that are used to cross-link a biopolymer that is produced by the MEOR bacteria.

SUMMARY OF THE INVENTION

Water-soluble viscosifying polymers are commonly used to enhance the recovery of petroleum from oil-bearing rock formations. Two methodologies used are "polymer drive" where a slug of injected polymer solution controls mobility of a waterflood and "profile modification" ("PM") wherein a polymer solution is injected and subsequently gelled in-situ within high permeability regions or "thief zones" so as to divert the waterflood into low permeability, oil-bearing zones. Commonly used polymers include polyacrylamide and xanthan, the latter a microbial polysaccharide produced in a fermentation plant. Common gellants for PM include polyvalent cations such as $Al^{+3}$ and $Cr^{+3}$.

Exisiting technology for PM has several problems, e.g., relatively high cost of the polymers, shear degradation of the polymer upon injection and difficulty of effectively delivering the gelation agent and controlling the gelation reaction.

In-situ production of extracellubar biopolymer by an injected microbe and its subsequent gelation solves these problems. The nutrient medium of the present invention favors production of biopolymer by the microbe from cheap substrates such as sucrose and allows precise delivery of a gelation agent and control of gelation. This medium, among other things incorporates a unique polyphosphate compound, a constitutent which serves several purposes: (1) it chelates cross-linking cations such as $Cr^{+3}$, allowing their incorporation in the medium; (2) it serves as a phosphorous source for growth and polymer production by the microbes, and in this process it is consumed; (3) as consumed, it releases the chelated cation, stimulating gelation of the polymer; and (4) it also chelates other cations present in the rock and connate water, e.g., $Ca^{+2}$, $Mg^{+2}$, or $Ba^{+2}$, which are inhibitory to polymer production by the microbe. The medium of our invention, containing controlled amounts of polyphosphate, permits optimum polymer production in-situ, facilitates delivery of gelation agent, and the gelation reaction at the correct time and place.

DETAILED DESCRIPTION OF THE INVENTION

MEOR requires the use of halotolerant, facultative anerobes since most oil field connate waters are salty and oxygen tension is nil. The cells (or spores from the cells) must be small-sized and mobile (or motile) so they can penetrate far into the porous rock. They must have non-fastidious nutrient requirements since laboratory culture media would be prohibitively expensive for field application where huge volumes are injected. The cells must be able to grow and produce the desire product under in-situ conditions of pH, temperature, heavy metal ion concentration, etc. Although some oil-bearing formations are too hot, impermeable or otherwise inhospitable to microbial presence, many are within a temperature range of 20°–80° C. and can support microbial presence and growth. Microbes used for MEOR must also be non-pathogenic and must not produce any animal or plant toxins, since they may be injected near water supply aquifiers.

Although many microbes can utilize hydrocarbons as the sole carbon and energy source, all known species that do this are aerobes which require molecular oxygen for the initial attack on hydrocarbons. If facultative anerobes are used for MEOR, non-petroleum carbon sources should be supplied. Unless hydrocarbon-utilizing anaerobes can be created through recombinant DNA techniques sufficient non-hydrocarbon metabolizable components must be present in the petroleum. Suitable carbon substrates are cheap carbohydrates such as molasses and whey and possibly inexpensive synthetic substrates such as methanol. Nitrogen, phosphorus and other nutrients must also be supplied if these are not present in the carbon substrate or in the rock. Nutrients must be supplied at the correct time that microbial activity is desired; loss or absorption of nutrients would be an economic debit. One notable problem with the addition of phosphates is that they may precipitate out of solution when injected downhole due to highly saline, acidic, or metal ion containing water. A typical liter of nutrient medium may comprise: 200 g sodium chloride; 0.5 g magnesium sulfate; 1.33 g ammonium nitrate; 2.0 g sodium nitrate; 1–5 g yeast extract; 2.6 g citric acid; plus 5–20 g of sodium tripolyphosphate as the phosphate source of the present invention.

Facultative anaerobic halophilic, or halotolerant, bacteria may be used to achieve profile modification through the production of an exopolymer and/or the growth of cells within highly permeable rock, thereby decreasing the permeability of this rock. The exopolymer forms an insoluble matrix within the rock pores which is resistant to bio-, shear, and thermal degradation. However, when bacteria produce a biopolymer it usually must be cross-linked with a metal ion so as to reduce water solubility and stabilize the polymer plug in zones of higher permeability.

POLYMER CROSS-LINKING

Once the MEOR bacterial cultures have been injected downhole, induced to grow, and then induced to form a polymer, a way must be found to keep the high molecular weight, but water soluble, material from being washed from, or degraded within the areas in which they are injected. This usually means cross-linking the polymer with metal ions.

Cross-linking is dependent on pH, temperature, monomer, and metal concentration, as well as a number of other factors. Metal ions that are useful in cross-linking include: aluminium (+3), titanium (+3), titanium (+4), ferric iron, chromium (+3) chromium (+6), cobalt (+2), cupric copper (+2), La (+3) and (+4), Fe (+3) molybdate and tungstate. Organic cross-linking agents may also be used, such as a polyamine produced by Gulf Oil Chemicals.

While it is encouraging that biopolymers react with a number of polyvalent metal ions to produce a more stable, cross-linked precipitate, the applicability of this knowledge to in situ application is questioned since the metal ion solutions are generally quite acid and they precipitate when neutralized. They may also exhibit a deleterious effect on the bacterial growth if they are freely present in too high a concentration.

POLYPHOSPHATE

However, metal ions can be kept in solution at a neutral pH when they are chelated with an inorganic polyphosphate, such as sodium tripolyphosphate (TPP). When complexed with tripolyphosphate (TPP), the metals are not available to react with the polymers or the bacteria. Thus, when TPP is added to the nutrient medium the bacteria may grow unencumbered and produce substantial quantities of biopolymer. At some point in time it will become necessary to release the metal ions to cross-link and gel the biopolymer (to plug the zones of high permeability). This is where the TPP acts in a multifaceted role. It is added for three purposes: to chelate the metal ions for the purposes described above; to provide a metabolizable source of phosphate to fit the growth requirements of the bacteria; and to resist precipitation out of solution (due to the presence of other metal ions that we found in connate water, i.e., $Ca^{+2}$ and $Mg^{+2}$). Therefore, the TPP is incorporated into the nutrient medium and may be injected downhole along with the bacteria and the metal ions that are used as biopolymer cross-linkers (it complexes these metal ions as well as connate water metal ions). As the bacteria grow they consume the TPP which releases the metal ions into the surrounding environment (as the TPP is depleted). As the metal ions are released they contact the biopolymer and cause it to gel and cross-link. An optimum concentration of TPP may be determined so that the chelation of the metal ions continues until such time when gelation of the polymer is desired and the adverse effects on the bacteria no longer matter.

One example of the preparation of a tripolyphosphate may be as follows, but this is in no way the only preparation that can be made. If $P_2O_5$, phosphorus pentoxide, is dissolved in $H_2O$, it reacts to form $H_3PO_4$, which is phosphoric or orthophosphoric acid. For example, $3H_2O + P_2O_5 \rightarrow 2H_3PO_4$. If additional $P_2O_5$ is added, it can react to form condensed chain-type structures where tripolyphosphate is the structure containing three phosphorus atoms:

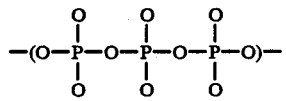

The tripolyphosphate anion forms salts such as sodium tripolyphosphate, $Na_5P_3O_{10} \cdot 6H_2O$. Tripolyphosphates (and other chain forms) are much better complexing agents for metal ions than an orthophsphate compound. They generally do not degrade very rapidly at alkaline pHs. Furthermore, the largest commercial application for polyphosphates is as a detergent builder where it serves to prevent ions that cause water hardness from precipitating a surfactant.

For a more in-depth discussion on polyphosphate compounds, see J. Van Wazer, Vol. I, Phosphorus and Its Compounds, Interscience Publishers (1958). This reference discusses methods of preparation, crystallization and identification of polyphosphates and is hereby incorporated by reference in its entirety.

EXAMPLE 1

Growth of Bacterial Isolates in Polyphsophate

A solution was prepared and named PM-2 which comprised: 200 g sodium chloride; 0.5 g magnesium sulfate; 1.33 g ammonium nitrate; 2.0 g sodium nitrate; 1 g yeast extract; 2.6 g citric acid and was adjusted to pH 8.0. Phosphate (as $KH_2PO_4$ or sodium tripolyphosphate) was added to PM-2 to give 5 or 10 g/l as indicated in Table I. The total volume of each tube was 35 ml. A 0.1 ml inoculum of either SL (NRRL No. B-18179) or Salton-1 (NRRL No. B-18178) was added to each tube. The results are in Table I.

TABLE I

| Medium having 3.5 ml PO4 | Growth | | | |
|---|---|---|---|---|
| | SLS | | Salton | |
| | 17 hr | 2 day visc. | 17 hr | 2 day visc. |
| PM-2 Control (with 10 g/l $KH_2PO_4$) | +++ | 4.2 | +++ | 3.02 |
| PM-2 with 5 g/l sodium tripolyphosphate and 5 g/l $KH_2PO_4$ | +++ | 4.06 | +++ | 4.24 |
| PM-2 with 5 g/l sodium tripolyphosphate | +++ | 1.9 | +++ | 2.8 |
| PM-2 with 10 g/l sodium tripolyphosphate and 5 g/l $KH_2PO_4$ | +++ | 5.66 | +++ | — |
| PM-2 with 10 g/l sodium tripolyphosphate | +++ | 4.02 | +++ | 3.40 |

EXAMPLE 2

Chelation of Ions in Connate Water

A solution of sodium tripolyphosphate was prepared in distilled water and the addition of a small amount of connate field water (with contained calcium and magnesium ions) caused a dense white precipitate to form. The addition of additional sodium tripolyphosphate caused the precipitate to dissolve.

To determine the amount of polyphosphate required to prevent precipitation of this field water, 10 ml of PM-2 nutrient medium was combined with varying amounts of polyphsophate and field water. For the results see Table II.

TABLE II

| 10 ml PM-2 (without PO4) plus: | Soluble | Amount of Field Water | Result |
|---|---|---|---|
| 0.05 g polyphosphate | Yes | 0.5 ml | ppt redissolved* |
| | | 1.0 ml | ppt remained |
| 0.15 g polyphosphate | yes | 1.0 ml | ppt redissolved* |
| | | 1.5 ml | ppt remained |
| 0.20 g polyphosphate | partially | 1.0 ml | ppt redissolved* |
| | | 1.5 ml | ppt remained |

*A precipitate initially formed, but was redissolved upon stirring.

EXAMPLE III

Growth of Bacterial Isolates in Crushed Berea

Salton and SL bacteria were added to PM-2 medium containing 5% sucrose. The phosphate source was either 10 g/1 $KH_2PO_4$ or sodium tripolyphosphate (as indicated below). Each culture tube was grown in the presence of 5 g crushed Berea sandstone.

TABLE III

| Additive | Phosphate | (0.1 ml) Inoculum | 3-day Growth | 3-day Viscosity |
|---|---|---|---|---|
| Crushed Berea | $KH_2PO_4$ | SLS | — | 0.96 |
| Crushed Berea | $KH_2PO_4$ | Salton | — | 1.2 |
| Crushed Berea | polyphosphate | SLS | ++++ | 2.62 |
| Crushed Berea | polyphosphate | Salton | ++++ | 4.0 |

EXAMPLE IV

Metal Ions as Cross-linking Agents for the Biopolymer

Purified, dialyzed solutions of biopolymer from SLS and Salton bacteria wre prepared and 10 ml was dispensed in each tube. The following metal ions were tested for cross-linking ability: Titanium in the +3 (as $TiCl_3$ or $TiOSO_4$) and +4 (as $TiCl_4$) valence state, Aluminum in the +3 (aluminum citrate) valence state, Chromium in the +3 ($Cr_2(SO_4)_3$) and +6 ($CrO_3$) valence state, Fe in the +3 ($FeCl_3$) valence state, Copper in the +1 ($CuSO_4$) valence state, and Cobalt in the +2 ($CoCl_2$) valence state. For the results see Table IV.

TABLE IV

| Metal Ion | Cross-linking | |
|---|---|---|
| | SLS Polymer | Salton Polymer |
| 300 ppm $Ti^{+4}$ ($TiCl_4$ used) | Yes | Yes |
| 300 ppm $Al^{+3}$ as citrate, adjusted to pH 6.2 | Yes/No | Yes/No |
| 116 ppm $Cr^{+3}$ as $Cr_2(SO_4)_3$ | Yes/No | Yes/No |
| 0.1 ml of 20% $TiCl_3$ | | Yes |
| 10 ml 20% $TiCl_3$ | Yes | Yes |
| 1 ml 0.2% $TiCl_3$ | Yes | Yes |
| 50 ml saturated $FeCl_3$ | Yes | Yes |
| 0.3 ml $Ti^{+3}$ as $TiOSO_4$ | Yes | Yes |
| 0.1 ml of 1% $CrO_3$ 0.0 ml 1N Thiourea | No | Yes |
| $Al(SO_4)_3$ | Yes | Yes |
| 0.5 ml of 1% $CoSO_4 \cdot 5H_2O$ | No data | Yes |
| 247 ppm $Co^{+2}$ (500 ml of 2% $CoCl_2$) | No data | Yes |

The use of TPP in a MEOR nutrient medium means that metal ions or other compounds (that are used to gel and stabilize a biopolymer) may be directly added to the microbial growth medium itself. It also means that the bacteria that are injected into a petroleum reservoir can be protected from the deleterious effects of the ambient metal ions while being able to use a form of phosphate that is not precipitated out of solution by these same ambient conditions.

Since many modifications and variations of the present invention are possible within the spirit of this disclosure, it is intended that the embodiments that are disclosed are only illustrative and not restrictive. Reference is made to the following claims rather than the specific description to indicate the scope of the invention.

What is claimed is:

1. A nutrient medium that is capable of flowing downhole into a petroleum reservoir and is capable of providing a metabolizable source of phosphate for microorganisms without precipitating on contact with connate water, said nutrient medium comprising a tripolyphosphate.

2. The nutrient medium of claim 1 wherein said tripolyphosphate is sodium tripolyphosphate, potassium tripolyphosphate, or ammonium tripolyphosphate.

3. The nutrient medium as recited in claim 2 further comprising metabolizable phosphate in forms that are not tripolyphosphates.

4. A nutrient medium to provide essential nutrients to induce bacterial spores to grow, replicate, and produce an exopolymer, comprising:

a metabolizable source of tripolyphosphate in a form so that the phosphate will not precipitate out of solution when the nutrient medium is flowed into a highly saline environment that has ions selected from the group consisting of alkaline earth, rare earth, transition and heavy metal ions, said phosphate compound being able to chelate polymer cross-linking agents that are deleterious to the growth of the bacteria; and sources for remaining metabolic requirements.

5. The nutrient medium of claim 4 wherein one liter of nutrient medium comprises an approximate amount of the following compounds:
   200 g sodium chloride;
   0.5 g magnesium sulfate;
   1.33 g ammonium nitrate;
   2.0 g sodium nitrate;
   1-5 g yeast extract;
   2.6 g citric acid; and
   5-20 g/liter Sodium tripolyphosphate;
   whereby the pH of said solution is adjusted to approximately 8.0.

6. The nutrient medium of claim 5 wherein inorganic sources of phosphate are also added that are nonpolyphosphates.

7. The nutrient medium of claim 5 wherein the concentration of sodium tripolyphosphate is 10 to 20 g/liter.

8. The nutrient medium of claim 4 wherein a polymer cross-linking agent is added, and wherein said cross-linking agent is selected from the group consisting of:
   (a) polyamide; and
   (b) ions of aluminum, chromium, titanium, lanthanum, cesium, iron, cobalt and copper.

9. The nutrient medium of claim 5 wherein a polymer cross-linking agent is added, and wherein said cross-linking agent is selected from the group consisting of:
   (a) polyamide; and
   (b) ions of aluminum, chromium titanium, titantiaum, lanthanum, cesium, iron, cobalt and coper.

10. The nutrient medium of claim 1 wherein the tripolyphosphate concentration is from 5 to 190 grams per liter.

11. The nutrient medium of claim 2 wherein the tripolyphosphate concentration is from 5 to 190 grams per liter.

12. The nutrient medium of claim 4 wherein the tripolyphosphate concentration is from 5 to 190 grams per liter.

* * * * *